United States Patent [19]

Thomas, Sr.

[11] Patent Number: 5,091,152
[45] Date of Patent: Feb. 25, 1992

[54] APPARATUS FOR ELECTRICALLY DESTROYING TARGETED ORGANISMS IN FLUIDS

[76] Inventor: Tim L. Thomas, Sr., 2350 Great Southwest Pkwy., Fort Worth, Tex. 76106

[21] Appl. No.: 195,752

[22] Filed: May 19, 1988

[51] Int. Cl.[5] .............................................. A61L 2/02
[52] U.S. Cl. ....................................... 422/23; 204/403; 204/412; 307/260; 307/261; 307/268; 324/448; 422/22; 422/186.04
[58] Field of Search ................................ 422/22–24, 422/186.04, 1, 28; 328/181, 178, 187; 307/261, 260, 268, 228; 204/412, 403; 324/448, 449

[56] References Cited

U.S. PATENT DOCUMENTS

| | | |
|---|---|---|
| 820,113 | 5/1906 | Hinkson . |
| 943,187 | 12/1909 | Hartman . |
| 1,020,001 | 3/1912 | Van Pelt . |
| 1,215,135 | 2/1917 | Fisher . |
| 1,382,158 | 6/1921 | Abogado ............................ 422/23 X |
| 1,440,091 | 12/1922 | Long . |
| 1,730,016 | 10/1929 | Rudd ................................. 422/22 X |
| 1,945,867 | 2/1934 | Rawls ................................ 422/22 X |
| 2,607,492 | 8/1952 | Anders . |
| 2,637,408 | 5/1953 | Yadoff .................................. 422/22 |
| 2,724,051 | 11/1955 | Rajchman et al. ................... 328/178 |
| 2,825,464 | 3/1958 | Mack . |
| 2,898,549 | 8/1959 | Miller ............................ 324/448 X |
| 3,068,694 | 12/1962 | Worswick . |
| 3,076,754 | 2/1963 | Evans . |
| 3,231,484 | 1/1966 | Berghaus .................... 422/186.04 X |
| 3,320,529 | 5/1967 | Vreeland et al. ............... 324/448 X |
| 3,340,175 | 9/1967 | Mehl . |
| 3,528,905 | 9/1970 | Miller . |
| 3,600,126 | 8/1971 | Hellund ................................ 422/23 |
| 3,637,482 | 1/1972 | Vajda . |
| 3,638,488 | 2/1972 | Meijer . |
| 3,697,877 | 10/1972 | Godfrey ......................... 328/187 X |
| 3,718,540 | 2/1973 | Bailey . |
| 3,753,886 | 8/1973 | Myers ............................... 422/23 X |
| 3,779,889 | 12/1973 | Loftfield . |
| 3,866,065 | 2/1975 | McIngvale ..................... 328/178 X |
| 3,951,807 | 4/1976 | Sanderson . |
| 4,062,754 | 12/1977 | Elbl . |
| 4,109,208 | 8/1978 | Tomisawa et al. ............. 328/178 X |
| 4,119,518 | 10/1978 | Miller et al. . |
| 4,121,991 | 10/1978 | Miller . |
| 4,193,859 | 3/1990 | King . |
| 4,284,906 | 8/1981 | Manfredi ....................... 328/181 X |
| 4,293,400 | 10/1981 | Liggett . |
| 4,407,719 | 10/1983 | Van Gorp . |
| 4,457,221 | 7/1984 | Geren ............................... 422/23 X |
| 4,458,153 | 7/1984 | Wesley ............................. 422/22 X |
| 4,642,165 | 2/1987 | Bier ...................................... 422/28 |
| 4,659,479 | 4/1987 | Stickler et al. . |
| 4,752,444 | 6/1988 | Bowen et al. ........................ 422/28 |

*Primary Examiner*—Robert J. Warden
*Assistant Examiner*—Amalia L. Santiago
*Attorney, Agent, or Firm*—Sughrue, Mion, Zinn, Macpeak & Seas

[57] ABSTRACT

The invention pertains to a method and apparatus for destroying a predetermined living organism in fluid, whereby a predetermined current having a specific waveform and frequency is applied to the fluid in order to destroy the predetermined living organism while it is in a chamber having a cylindrical first electrode, a second rod-shaped electrode and a cylindrical third electrode disposed between said first and said second electrodes. The first, second and third electrodes all have a common axis.

18 Claims, 5 Drawing Sheets

APPARATUS FOR ELECTRICALLY DESTROYING TARGETED ORGANISMS IN FLUIDS

BACKGROUND OF THE INVENTION

1. Field of the Invention

The present invention relates to a method and apparatus for electronically sterilizing fluids by destroying living organisms without adding chemicals or boiling the fluids to destroy these organisms.

The presence of microorganisms in liquids is undesirable in a variety of circumstances, for example, swimming or drinking water, milk, or blood, to name only a few. A number of methods have been developed to destroy these microorganisms.

Most potable water supplies utilize chlorination (chlorine additives) to destroy harmful organisms in the water in order to make water safe for human consumption. Heating a liquid until it reaches its boiling point is another common way to purify liquids. Likewise, water that is contaminated by microorganisms may be purified by adding silver or copper ions through the use of consumable silver or copper electrodes. Each of these methods for purifying liquid has drawbacks.

The addition of chemicals such as chlorine additives is an expensive process which requires large amounts of these chemicals in order to purify a significant amount of the liquid. A side effect of this process is that the chlorine additives, which remain in the liquid, themselves can have harmful effects depending upon the ultimate end use of the liquid. For example, adding chemicals to a sample of blood in order to kill a specific microorganisms may render the sample of blood useless, as the chemicals required to kill the microorganism can themselves be harmful or can cause mutation of the blood cells themselves and thus render the sample toxic while destroying the targeted microorganism.

Boiling a liquid like the addition of chemicals, is an expensive process, requiring the expenditure of a great deal of energy in order to process significant quantities of liquid. An additional drawback is that a great deal of time is needed to heat large quantities of liquid to their boiling point, thus limiting the amount of liquid that can be processed.

Finally, the addition of silver or copper ions through the use of consumable silver or copper electrodes requires complicated apparatus that is expensive and extremely liable to break down. The metal electrodes used to introduce the ions into the liquid have to be cleaned or completely replaced very frequently.

The present invention eliminates the need for chemical additives, such as chlorine, which can alter the basic $H_2O$ content, boiling to remove the threat of harmful organisms, or the addition of metallic ions.

SUMMARY OF THE INVENTION

An object of the present invention is to provide a method and apparatus for electrically destroying microorganisms in liquids in which the disadvantages described above do not occur and which provides the ability to target specific microorganisms for elimination.

Another object is to provide a method and apparatus for electrically destroying microorganisms wherein it is possible to target a specific microorganism for destruction.

A still further object is to provide a method and apparatus wherein the destruction of a specific microorganism is conducted by adjusting the current, frequency and waveform applied to the fluid containing the microorganism.

These and other objects are accomplished by providing a method and apparatus in which a predetermined current having a specific waveform and frequency is applied to the fluid in order to destroy the organism, while the fluid is in a chamber having a cylindrical first electrode, a second rod-shaped electrode and a cylindrical third electrode disposed between the first and second electrodes. The first, second and third electrodes all have a common axis.

DESCRIPTION OF THE PREFERRED EMBODIMENT

According to the present invention, targeted organisms in a static or flowing state are destroyed using electrical methods according to the following expression:

$$Td(cOx) = f(I:F:Wf)ps$$

where cOx is the targeted organism to be destroyed, I is the current required, F is the alternating frequency required and Wf is the waveform of the current required to destroy (Td) the identified organism. In an exemplary example, E. Coli (cOx) is used as a target organism.

By employing proper values of I, F and Wf, total destruction of the target organisms (Td) may be achieved. For other target organisms, virus strains, etc., the expression would be:

$Td(xOx)=f(I:F:Wf)$ where xOx is the target organism other than *E. Coli.*

Figure 1A:
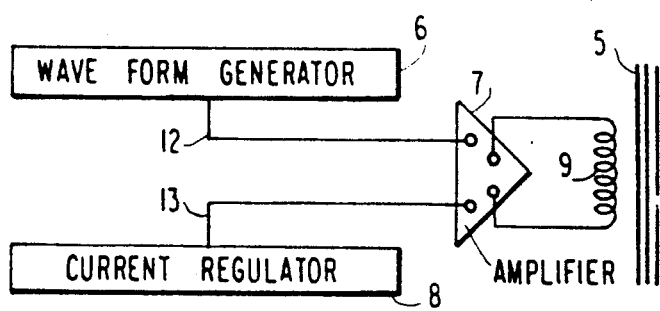
FIG. 1 is a longitudinal section and a cross section showing a first embodiment of an apparatus according to the present invention.
Figure 1B:
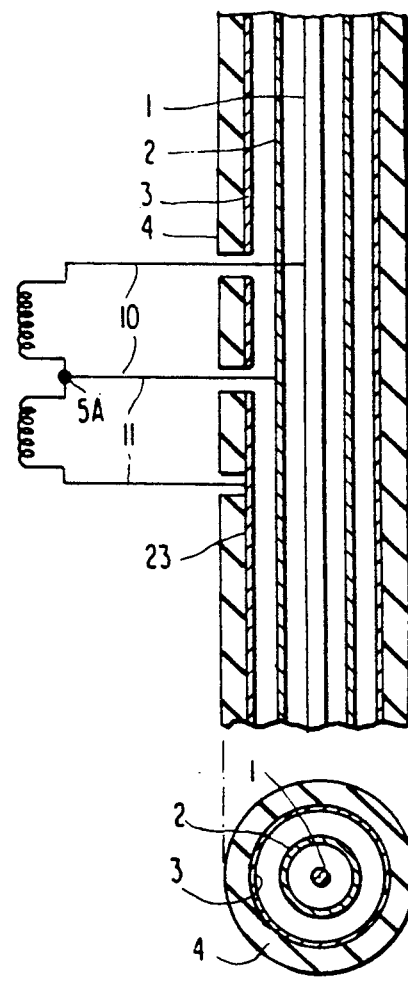
Figure 8:
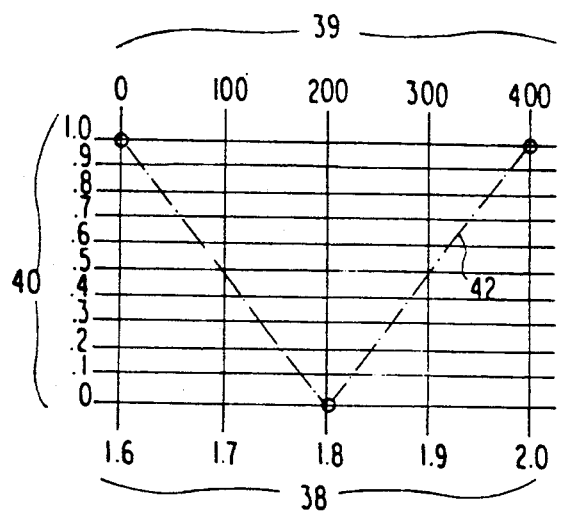
FIG. 8 is an enlarged portion of FIG. 4.

FIGS. 1A and 1B show longitudinal and cross-sectional view of an apparatus according to a first embodiment of the present invention. As shown in FIGS. 1A and 1B, the apparatus has a central electrode 1, a middle electrode 2, and an outer electrode 3, each of which is made of electrical conducting metals. Both the middle electrode 2 and outer electrode 3 are cylindrical conductive conduits, while the central electrode 1 is solid core. The central electrode 1 is disposed in the center of the middle electrode 2 and parallel to axis of the cylinder of the middle electrode 2. The outer electrode 3 surrounds the middle electrode 2, and the two electrodes share a common axis. These electrodes combine to provide a push pull current charge to the chamber from the alternating current supplied by the transformer 5.

The ends of the chamber defined by the electrodes 1, 2 and 3, are open in order to permit the flow of fluid through the chamber. While the fluid flows through the chamber, it is subjected to a current having a specific power, frequency and waveform in order to destroy a targeted living organism in the flowing fluid.

The center electrode 1 is positive relative to the current induced in the chamber. while the outer electrode 3 is negative relative to the current induced in the chamber. The middle electrode 2 which is connected to center tap 5A is neutral relative to this current, but has a potential which is insulated so that it is above ground in a push-pull configuration, i.e., the power 10 supplied to the inner area between the inner electrode 1 and the middle electrode 2, and the power 11 supplied to the outer area between the middle electrode 2 and the outer electrode 3 are balanced.

An insulating conduit 4 is provided outside of the outer electrode 3, in order to assure the electrodes 1, 2 and 3 will float the currents imposed on the chamber, above earth ground.

A sealant 23 is disposed between the outer electrode and the insulating conduit 4 to ensure that the flowing stream of liquid remains within the boundaries of the inner area and outer area between the middle electrode 2 and the outer electrode 3.

A waveform generator 6, and a current regulator 8 are provided. The outputs of the waveform generator 6 and the current regulator 8 are supplied to an amplifier 7.

The waveform generator 6 is capable of providing a variable frequency output in a sine, square, pulsed negative-pulsed positive triggered, or saw tooth waveform output 12, so that the targeted organism in inner area 33 and outer area 34, as shown in FIG. 2. can be destroyed.

The amplifier 7 is an AC current generator with a single phase output 9 that couples the current output of the amplifier 7 through the transformer 5 in a balanced push pull connection to chamber areas 33 and 34.

The current regulator 8 senses the resistivity of the fluids in the chamber and acts as a feedback to the amplifier 7 in order to maintain a predetermined current in the chambers 33 and 34. that is required to destroy the targeted organism.

As shown in FIG. 1B, a power supply 17 is provided which is capable of AC or DC operation. or in an uninterrupted configuration. The power output path to the waveform generator 6, the current regulator 8 and the power amplifier 7 are shown as 14.

In order to equalize the current flow in the chamber shown in FIG. 1. which is defined as the areas 33 and 34 in FIG. 2. the areas 33 and 34 must be equal to one another.

The inner chamber 33 is comprised of the area between the inside diameter of the cylindrical conductor 2 which has a radius $r_{21}$ and the solid center rod 1 which has a radius of $r_{22}$. Therefore, the area of the inner chamber 33 is computed as $\pi r_{21}^2-\pi r_{22}^2$.

The outer chamber 34 is comprised of the area between the inside diameter of the outer cylindrical electrode 3 which has a radius $r_{18}$, and the outside diameter of the inner cylindrical electrode 2 which has a radius $r_{19}$. Therefore, the area of the outer chamber 34 is computed as $\pi r_{18}^2-\pi r_{19}^2$.

The ratio of the area between chambers 33 and 34 is 1:1. The variables are $r_{18}$, $r_{19}$, $r_{21}$ and $r_{22}$. Thus in order for the areas in the two chambers to be equal. the following function must be satisfied: $\pi r_{21}^2-\pi r_{22}=\pi r_{18}^2-\pi r_{19}^2$.

As shown in FIG. 3, the output of the transformer 5 is connected to the electrodes 1 2 and 3 by 10 and 11 through the insulating conduit 4. The inner electrode 1 is longer than the middle electrode 2 and as a result projects out of the middle electrode 2 along its axis, as shown in FIG. 3. Likewise, the middle electrode 2 is longer in the axial direction than the outer electrode 3, and thus projects out of the outer electrode 3.

Thus, the output of the transformer may be connected to the inner electrode 1 at a point where it projects out of the middle electrode. and to the middle electrode at a point where it projects out of the outer electrode. The outer electrode 3 is connected directly through a hole in the insulating conduit 4 and sealant 23. As a result of this configuration it is not necessary to penetrate through an electrode to reach an electrode located radially inwards, and thus a larger surface insulating area is possible between the connections.

EXAMPLE 1

The chart shown in FIG. 4 represents the progressive destruction of *E. Coli* suspended in tap water which has been boiled to remove active chlorine but retain dissolved impurities normally present in usual water supplies. As the frequency is increased from 60 to 2.000 Hz along the abscissa, the waveform and current input to the chamber, as shown in FIG. 5, are held constant. Partial destruction of the *E. Coli* organisms occurred between 400 and 800 Hz. Maximum destruction occurred between 1,600 and 2,000 Hz. Thus, the efficient and maximum destruction of the targeted *E. Coli* organisms was between 1,600 and 2000 Hz. The destruction of the *E. Coli* at the point 28 in FIG. 4 represents a 100% destructi ratio as only 60% of the *E. Coli* cultures were exposed in the areas 33 and 34 shown in FIG. 3 of the chamber. The destruction of the *E. Coli* at point 29 indicates a 100% destruction ratio. This is attributable to the static state of the fluids in the chamber and the natural mix of the same culture content as five runs and draws were conducted in the same fluid. Between 800 and 1,200 Hz an apparent dormant state of *E. Coli* was achieved.

The waveform shown in FIG. 5 approximates a square wave used as the Wf factor in the destruction of the E. Coli organisms. The amplitude 26 represents 350 vAc@350 mA input to the chamber shown in FIG. 1 in both longitudinal and cross section. and in FIG. 8 in detail. When a pure sine waveform was applied to the apparatus shown in FIG. 7, the E. Coli was not affected and the amount of live cultures exiting the apparatus equaled the amount of live cultures entering the opposite end.

Figure 1B:
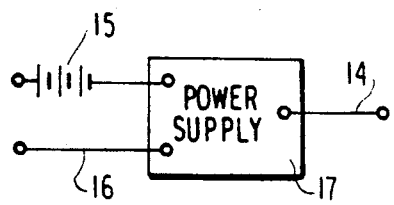
Figure 6A:
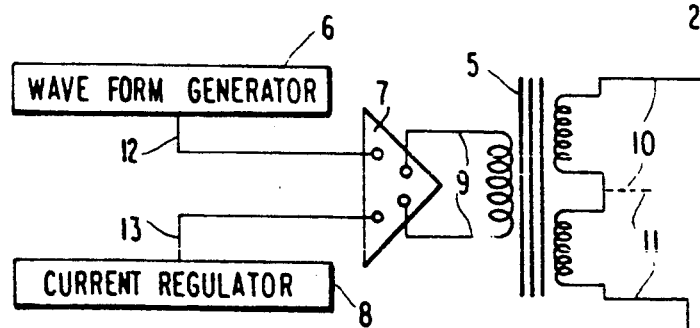
FIGS. 6A and 6B are longitudinal section showing a second embodiment of an apparatus according to the present invention.
Figure 6B:
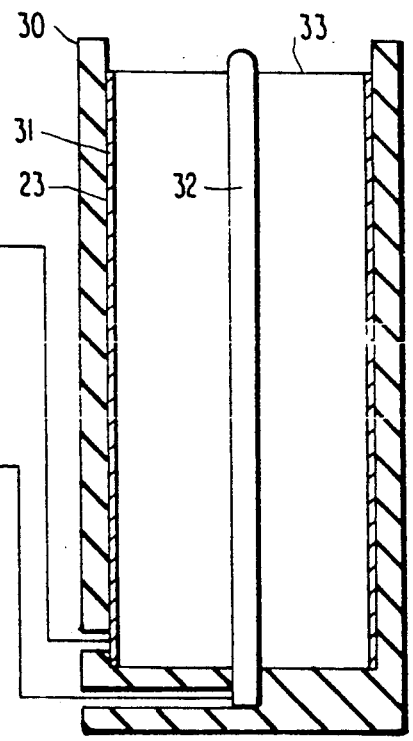

FIGS. 6A and 6B show a second embodiment of the present invention. In this embodiment, the power supply 17. waveform generator 6, current regulator 8, amplifier 7 and transformer 5 are configured as shown in FIG. 1, except that the output of the transformer 5 is connected to the chamber in a single ended output arrangement with the center tap (at 10 and 11) not used. This embodiment is for static sterilization purposes using a two electrode chamber.

Figure 6B:
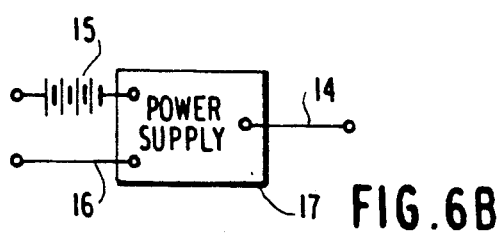

In the chamber shown in FIG. 6 the area where the targeted organisms in the liquid are to be destroyed is referenced as 33. The outer container 30 is made of a non-conductive material. An outer cylindrical electrode 31 is disposed just inside the container 30. Inner electrode 32 is similar to the inner electrode 1 of FIG. 3. Once again, a sealant 23 is used to bond outer electrode 31 to the container 30. A chamber of this type can be used in laboratory research into the destruction of other types of organisms other than E. Coli.

Figure 2:
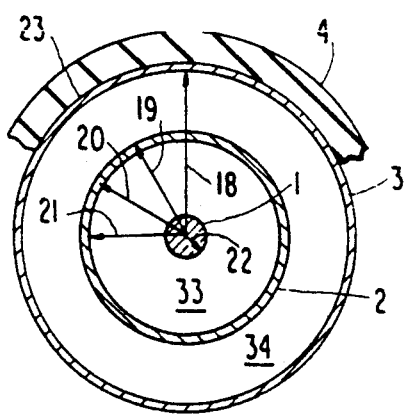
FIG. 2. shows a method of equalizing the cross sectional areas of the chambers of the apparatus shown in FIG. 1.
Figure 3:
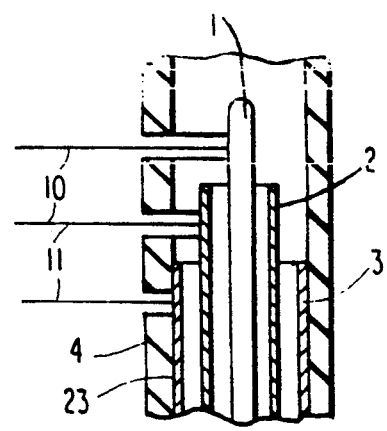
FIG. 3 is a longitudinal section illustrating the power connections in the apparatus shown in FIG. 1.
Figure 7:
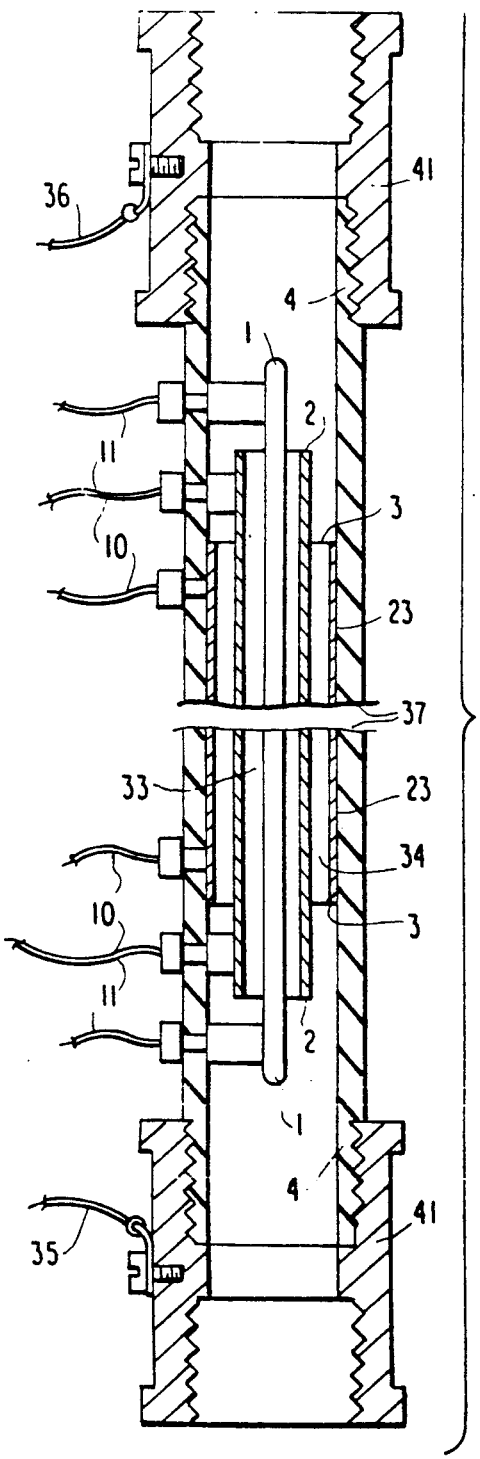
FIG. 7 is a longitudinal section showing an apparatus according to the first embodiment which has couplings to allow for constant fluid flow and means for detecting faults.

FIG. 7 shows the apparatus of FIGS. 1 and 3 which has couplings to allow for constant fluid flow and means for detecting faults. The actual areas where organisms are destroyed are within the confines of electrodes 1, 2 and 3, areas 33 and 34 in FIG. 2. Power is supplied to the chamber through parallel connections 10 and 11 at both ends of the chamber. The connections to the electrodes 1 and 2 are rigid in order to accurately locate the electrodes relative to one another and the outer electrode 3.

The resistivity of the fluids in the chamber areas 33 and 34 compromise the balances load placed on the output of the transformer 5, as shown in FIG. 1. Thus, in the equation e/Ir, the fluids in the chamber are "r" while "e" is the voltage applied related to the current I required for destruction of the target organism.

PVC schedule 40 material may be used as the material for the insulating conduit 4. The insulating conduit 4 acts as a base for the connections to the electrodes. Sealant 23 between the insulating conduit 4 and the outer electrode 3 is required to prevent any organisms in the fluids from escaping the electrified areas of the chamber, 33 and 34, in a path between the outer electrode 3 and the insulating conduit 4. Fluid may flow in either direction through the chamber shown in FIG. 8, as the direction of fluid flow has no effect on the destruction process.

End connections 41 are provided at either end of the chamber and are made of conducting metal in order to provide coupling to, external piping as might be required. In addition, to providing a means for coupling, the end connections 41 are provided with outputs 35 and 36 at either end, to detect any leakage of current from electrodes 1, 2 and 3 to the flow of liquid in the chamber beyond the input or output stream of the fluid.

Figure 10:
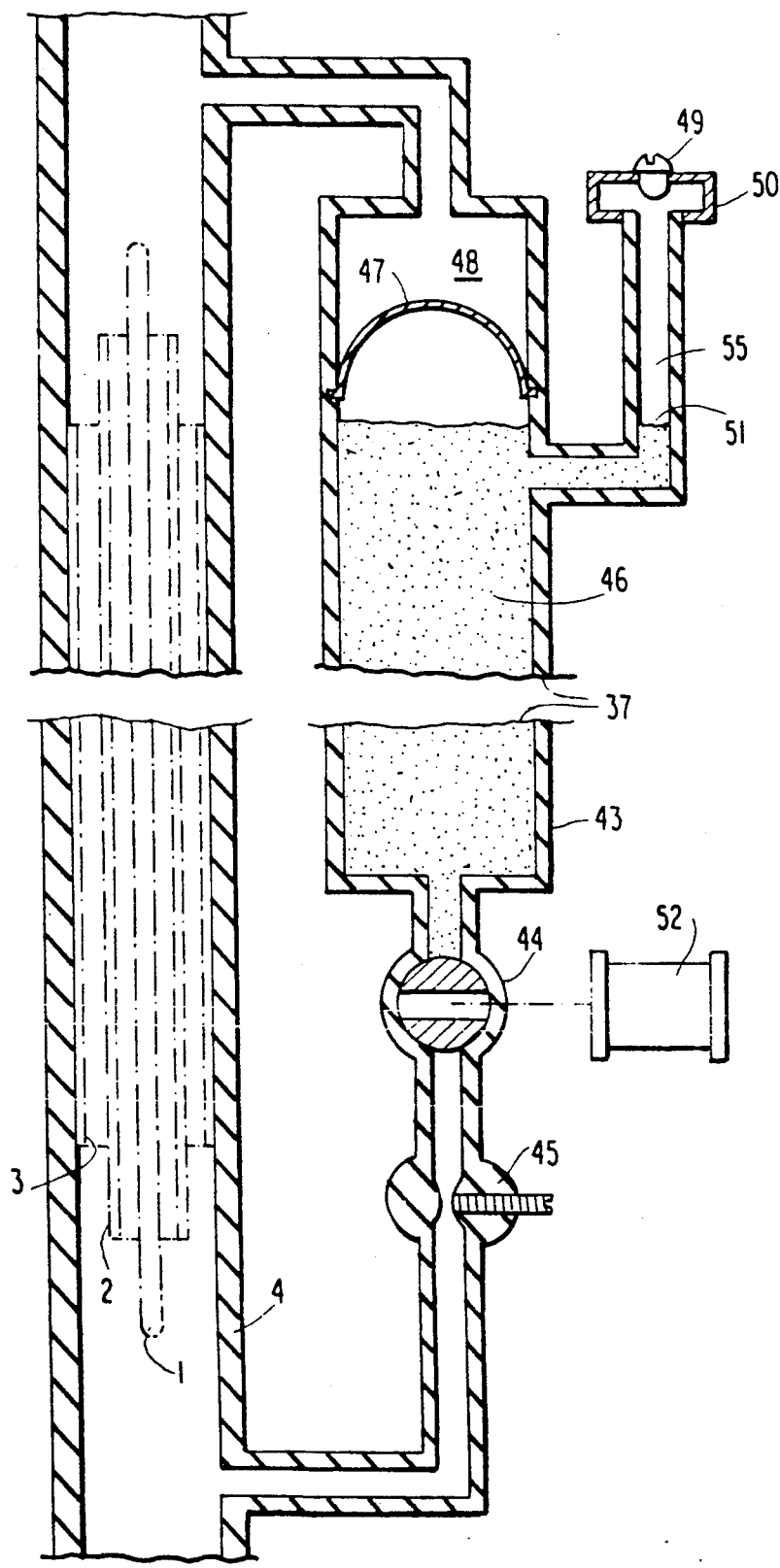
FIG. 10 is a longitudinal section of a fail safe apparatus for the apparatus according to the present invention in the event of power or component failure.

The outputs 35 and 36 are connected to ground and current fault detector circuits in the amplifier section of the apparatus shown in FIG. 6. Upon detection of faults, alarm outputs are activated and power to the chamber is disconnected. Upon fault detection the apparatus shown in FIG. 10 is activated if required.

The length of the chamber depends on the requirements of the particular fluid and the targeted organism.

i.e., the necessary gallons per hour of flow required and the power input to the chamber required for destruction of the target organism. The total length of the chamber as shown in FIGS. 1, 2, 3, 6, 7, 9 and 10 is not shown and the jagged lines 37 represent the removed central portion.

Figure 4:
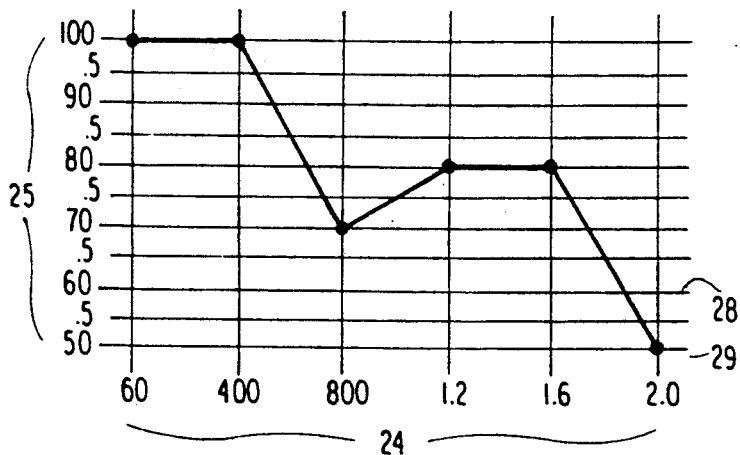
FIG. 4 is a chart representing the progressive destruction of E. Coli in water, where the ordinate is the destruction ratio and the abscissa is frequency.
Figure 5:
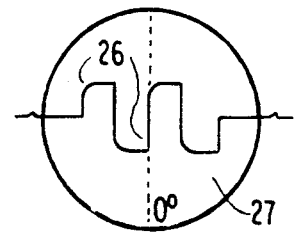
FIG. 5 shows the waveform and amplitude used to destroy the E. Coli organism shown in FIG. 4.

FIG. 8 is an enlarged portion of FIG. 4, in the 400 Hz range between 1,600 and 2000 Hz. As shown, 100% destruction of the target organism, E. Coli in potable water, occurred at approximately 1,800 Hz, with a waveform and amplitude of the type shown in FIG. 5. 1.0 on the ordinate represents a 100,000 count of E. Coli culture. "O" on the ordinate represent a zero count, and thus a 100% destruction of the target organism in the chamber in the areas 33 and 34. The LD (lethal dose corresponding to total destruction of the targeted organism) is achieved between 1,600-2,000 Hz.

Figure 9:
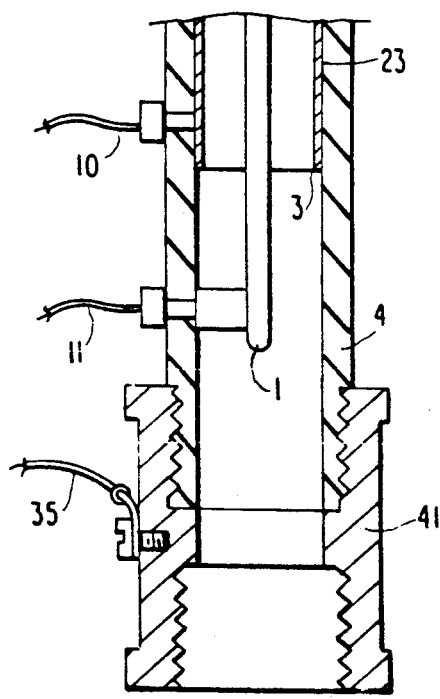
FIG. 9 is a longitudinal section showing a third embodiment of an apparatus according to the present invention.

A third embodiment of the present invention is shown in FIG. 9, wherein the middle electrode 2 shown in FIG. 7 is not required to target certain organisms. Rodephria, an organism found in most pond, stream or river water, is a case in point for the use of this embodiment. Other organisms where relatively small currents along with a proper waveform are necessary, may also be destroyed in such an apparatus.

As shown in FIG. 11, the destruction of the target organism Rodephria occurred at less than 50 $\mu$A using the frequency and waveform shown, in a chamber having a configuration shown in FIG. 9.

FIG. 10 shows a fail safe means to chemically sterilize flowing fluids in the event of power or component failure in the chamber shown in FIGS. 1, 2, 3, 7 or 9. Upon detection of electrical component or power failure causing the electrodes to fail to deliver the required current with the proper waveform to destroy the target organisms, the valve 44 which is normally closed, would open due to an interruption of the current to solenoid 52. When valve 44 is opened liquid chemicals (chlorine for example) flow through regulator valve 45 and then on into the main stream of the liquid flow.

A container 43 stores the chemicals 46, and pressure is imposed on the chemicals 46, caused by the normal fluid flow exerting pressure on the diaphragm 47 which in turn applies pressure against the valve 44.

A filling tube 55 is provided in order to permit replacement of chemicals. The filling tube 55 has a cap 50 equipped with a pressure type check valve 49 to enable the chemicals to flow in the absence of pressure from the fluids in the flowing or static state, 51 indicates the normal level of chemicals 46.

An absence of pressure on the diaphragm 47 would cause the check valve to open, thereby breaking any vacuum that would restrict the flow of the chemicals 46 in container 43. As indicated by 37 the container may be of any required size so that it can contain enough chemicals 46 to ensure sterilization of the fluids during prolonged power or component outage.

EXAMPLE 2

FIG. 11 shows the relationship between the current I, the frequency F and the waveform Wf needed for the total destruction, Td, of the target organism Rodephria, and is in agreement with the expression:

$$Td(rOx) = f(I:F:Wf)$$

where rOx is the target organism Rodephria, I is the current imposed on the fluids containing the organism, F is the frequency of the current and Wf the waveform of the frequency. All of these variables are combined in proper values to completely destroy, Td, the target organism in fluids. The fluid contained both rodephria and daphneia organisms, but rodephria was the organism targeted for destruction.

The destruction of Rodephria organisms is shown in chart 74 (FIG. 11C) where the target organism is shown as alive by the number 1.0 on the ordinate, and as completely destroyed as 0 on the ordinate. Thus, according to the above noted formula for the destruction shown in chart 74:

Td: I=50 μA
F=360 Hz
Wf=Triangle (sawtooth)
Ox: Rodephria organism.

Figure 11A:
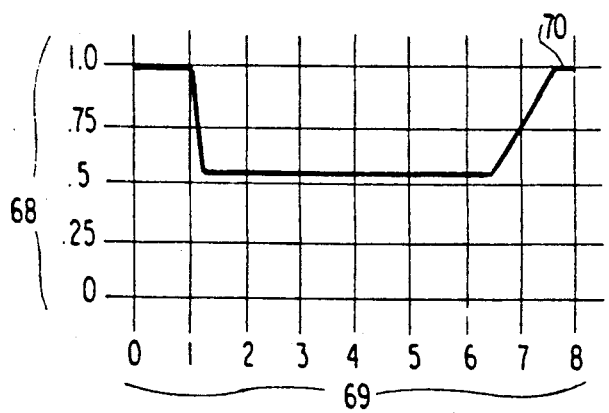
FIGS. 11A and 11C are charts representing the progressive destruction of Rodephria and Daphneia in water, where the ordinate is the destruction ratio and the abscissa is time.
Figure 11B:
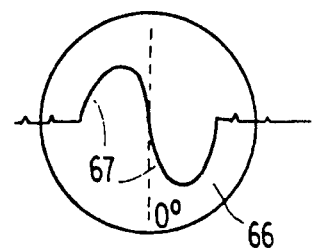
FIGS. 11B and 11D are the corresponding waveforms which were applied in these cases.
Figure 11C:
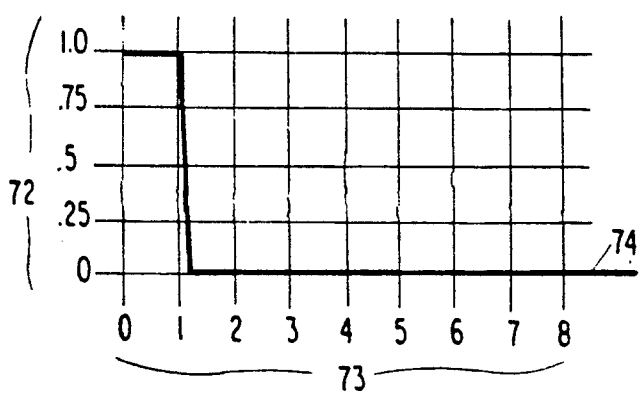
Figure 11D:
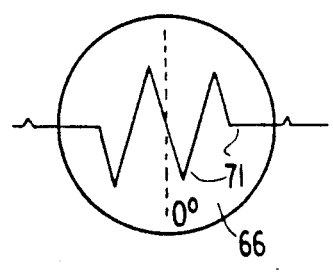

For all practical purposes, the destruction of the Rodephria organism is instantaneous, as shown on the chart 74 and the destruction remains complete. There is no revival as shown on the chart 70 (FIG. 11A), which is also directed to rodephria as the target organism. The triangular waveform Wf is shown on the oscilloscope 66 as 71 (FIG. 11D).

Also shown, in the chart 70 (FIG. 11A) is a target organism rodephria which was subjected to 50 μA at a frequency of 360 Hz and a sine waveform 67. The target organism rodephria was rendered inactive, or dormant, when in the same chamber with the daphneia organism for a period of nearly 8 hours, before resuming an active state. It is assumed that with further shifting of I, F and Wf. the results would be reversed, wherein the daphneia would be destroyed and the rodephria would be rendered inactive for a period time.

In further support of the fact that a proper combination of I, F and Wf can target living organisms, the rodephria and daphneia organisms were subjected to a change in waveform. as shown on the oscilloscope 66. While the waveform was a sine wave the other values in the equation remained the same, and the rodephria organisms were rendered dormant and not destroyed as shown in chart 70. When the waveform was changed from the sine waveform 67 to the sawtooth waveform 71 (FIG. 11D), total destruction of the rodephria was achieved, as opposed to the period of dormancy which resulted from the sine waveform 67.

Figure 12:
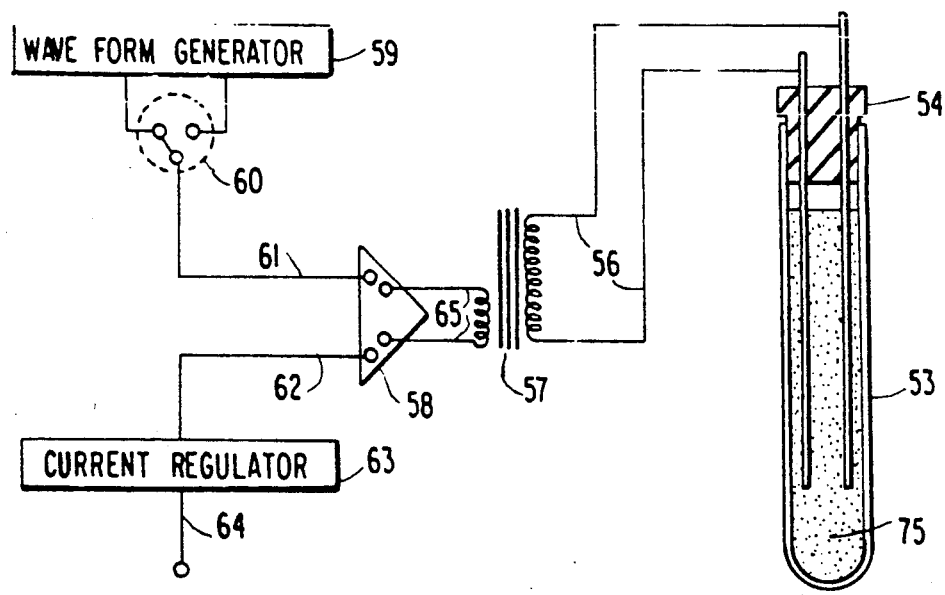
FIG. 12 is a longitudinal section showing another embodiment of the invention.

FIG. 12 shows an embodiment which is similar to the previous embodiments. As shown in FIG. 12, the apparatus includes electrode 56 connected to a standard test gube 53 containing fluid 75 via a conventional stopper 54. As in the previous embodiments, the electrodes 56 are connected to an amplifier 58 having output 65 via transformer 57. Input drive to the amplifier 58 is shown as a wave form generator 59 connected to amplifier 58 via switch 60 and output lead 61. A current regulator 63 having input 64 is connected to the amplifier 58 via output lead 62.

I claim:

1. Apparatus for destroying a predetermined living organism in a fluid comprising:
   A. C. current generating means for generating an A.C. current having a predetermined magnitude, frequency and wavform being selected to destroy a predetermined living organism;
   a chamber for containing a fluid having the predetermined living organism therein, said chamber comprising a first cylindrical electrode disposed in said chamber, a second rod-shaped electrode disposed in said chamber and along a central axis of said first cylindrical electrode, and a cylindrical third electrode, disposed between said first and second electrodes, which is connected to said A.C. current generating means, said first cylindrical and second rod-shaped electrodes each being connected to receive said current generated from said A.C. current generating means.

2. An apparatus for destroying a predetermined living organism in fluids as claimed in claim 1, wherein said chamber further comprises:
   an insulating means for insulating said electrodes, said insulating means being disposed on the outside of said first electrode; and
   sealant means for bonding said insulating means and said first electrode.

3. An apparatus for destroying a predetermined living organism in fluids as claimed in claim 1, wherein said predetermined current is supplied by transformer means.

4. An apparatus for destroying a predetermined living organism in fluids as claimed in claim 3, wherein said A.C. current generating means comprises:
   A.C. current waveform generator means for generating a plurality of waveforms with variable frequency and magnitude;
   current regulator means for sensing the resistivity of the fluid and for maintaining the predetermined current;
   amplifier means, connected to receive the outputs of said waveform generator means and said current regulator means, for providing an amplified current;
   power supply means for supplying power to said waveform generator means, said current regulator means, said amplifier means and said transformer means; and
   a first connecting means for connecting an output of said transformer means to said first electrode;
   wherein said transformer means receives the output of said amplifier means, said transformer means is connected to said second electrode through said support means, and said current output from said transformer means is controlled by said waveform generator means and said current regulator.

5. A apparatus for destroying a predetermined living organism in fluids as claimed in claim 1, wherein said chamber has a shape so as to allow the fluid to flow therethrough while said predetermined current is supplied.

6. An apparatus for destroying a predetermined living organism in fluids as claimed in claim 5, wherein said chamber has first and second ends, and wherein the apparatus further includes means for coupling oen of the first and second chamber ends to external piping.

7. An apparatus for destroying a predetermined living organism in fluids as claimed in claim 1, wherein said chamber has a shape so as to allow the fluid to remain static in said chamber while said current is supplied.

8. An apparatus for destroying a predetermined living organism in fluids as claimed in claim 7, wherein said chamber has first and second ends, and wherein one of said chamber ends is sealed.

9. An apparatus for destroying a predetermined living organism in fluids as claimed in claim 1, wherein said first, second and third electrodes have a common axis said common axis being said central axis.

10. An apparatus for destroying a predetermined living organism in fluids as claimed in claim 9, wherein said first, second and third electrodes are disposed such that the cross sectional area between the first and second electrodes on a plane perpendicular to said common central axis is equal to the cross sectional area between said third and second electrodes in said plane.

11. An apparatus for destroying a predetermined living organism in fluids as claimed in claim 9, wherein said chamber has a shape such that the fluid flows through said chamber while said current is supplied.

12. An apparatus for destroying a predetermined living organism in fluids as claimed in claim 11, wherein said chamber has first and second ends, and means for coupling one of said chamber ends to external piping.

13. An apparatus for destroying a predetermined living organism in fluids as claimed in claim 9, wherein said chamber has a shape such that the fluid remains static in said chamber while said current is supplied.

14. An apparatus for destroying a predetermined living organism in fluids as claimed in claim 9, whereins aid A.C. generating means comprises:
   A.C. Current waveform generator means for generating a pluraltiy of waveforms with variable frequency and magnitude;
   current regulator means for sensing the resistivity of a fluid and for maintaining the predetermined current;
   amplifier means, connected to receive the outputs of said waveform generator means and said current regulator means, for providing an amplifier current;
   transformer means for supplying a predetermined current;
   power supply means for supplying power to said waveform generator means, said current regulator means, said amplifier means and said transformer means; and
   a first connecting means for connecting a first output of said transformer means to said first electrode;
   wherein said transformer means receives the output of said amplifier means, said transformer means is connected to said second and third electrodes, and a current output form said transformer means is controlled by said waveform generator means and said current regulator means.

15. An apparatus for destroying a predetermined living organism in fluids as claimed in claim 14, wherein said third electrode is connected to a center tap of said transformer means.

16. An apparatus for destroying a predetermined living organism in fluids as claimed in claim 9, further comprising a fail safe means for detecting at least one of a power failure and an electric component failure, said fail safe means including chemical adding means operable in response to said detection, for adding chemicals to the fluid to ensure destruction of said predetermined microorganism.

17. An apparatus for destroying a predetermined living organism in fluids as claimed in claim 16, wherein said fail safe means comprises:
   container means for containing said chemicals;
   detecting means for detecting a power failure, and producing a current as longa s no power failure is detected;
   valve means connected to said container means for permitting said chemicals in said container means to discharge;
   a solenoid means for activating said valve means when said current from said valve means is interrupted; and
   regulator valve means for regulating the flow of said chemicals.

18. An apparatus for destroying a predetermined living organism in fluids as claimed in claim 17, whereins aid fial safe means further comprises:
   diaphragm means in said container means for imposing pressure on said chemicals in said container means, said pressure being exerted by the normal flow of said fluid containing said predetermined living organism through said container means.

* * * * *